United States Patent
Gee et al.

(10) Patent No.: US 10,314,638 B2
(45) Date of Patent: Jun. 11, 2019

(54) ARTICULATING RADIO FREQUENCY (RF) TISSUE SEAL WITH ARTICULATING STATE SENSING

(71) Applicant: Ethicon Endo-Surgery, LLC, Guaynabo, PR (US)

(72) Inventors: Jacob S. Gee, Cincinnati, OH (US); David C. Groene, Cincinnati, OH (US); Nicholas G. Molitor, Milford, OH (US); Emily H. Monroe, George's Mills, NH (US)

(73) Assignee: Ethicon LLC, Guaynabo, PR (US)

( * ) Notice: Subject to any disclaimer, the term of this patent is extended or adjusted under 35 U.S.C. 154(b) by 683 days.

(21) Appl. No.: 14/680,765

(22) Filed: Apr. 7, 2015

(65) Prior Publication Data
US 2016/0296268 A1    Oct. 13, 2016

(51) Int. Cl.
*A61B 18/14*    (2006.01)
*A61B 18/08*    (2006.01)
(Continued)

(52) U.S. Cl.
CPC ........ *A61B 18/085* (2013.01); *A61B 18/1445* (2013.01); *A61B 2017/00389* (2013.01);
(Continued)

(58) Field of Classification Search
CPC .............. A61B 18/085; A61B 18/1445; A61B 2017/00389; A61B 2018/0063; A61B 2018/00916; A61B 2018/00922
See application file for complete search history.

(56) References Cited

U.S. PATENT DOCUMENTS 2,366,274 A    1/1945 Luth et al.
2,458,152 A    1/1949 Eakins
(Continued)

FOREIGN PATENT DOCUMENTS

CN    1634601 A    7/2005
CN    1640365 A    7/2005
(Continued)

OTHER PUBLICATIONS

Abbott, et al. Proceedings of the 2007 IEEEIRDJ International Conference on Intelligent Robots and Systems. 410-416, 2007.
(Continued)

*Primary Examiner* — Thomas A Giuliani
*Assistant Examiner* — Tigist S Demie

(57) ABSTRACT

A surgical instrument is presented that may include a handle assembly, a shaft assembly, an end effector and an articulation joint coupled to the shaft assembly and the end effector. The surgical instrument also may include an articulation control mechanism configured to: control movement of the articulation joint between a first and second maximum articulation angle; determine that the articulation joint has articulated to the first maximum articulation angle; provide a first indication that the articulation joint has articulated to the first maximum articulation angle; determine that the articulation joint has articulated to the second maximum articulation angle; and provide a second indication that the articulation joint has articulated to the second maximum articulation angle.

15 Claims, 10 Drawing Sheets

(51) Int. Cl.
*A61B 17/00* (2006.01)
*A61B 18/00* (2006.01)
(52) U.S. Cl.
CPC ............. *A61B 2018/0063* (2013.01); *A61B 2018/00916* (2013.01); *A61B 2018/00922* (2013.01)

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,190,541 A | 3/1993 | Abele et al. |
| 5,196,007 A | 3/1993 | Ellman et al. |
| 5,205,459 A | 4/1993 | Brinkerhoff et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,257,988 A | 11/1993 | L'Esperance, Jr. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |

(56) References Cited

U.S. PATENT DOCUMENTS

| | | |
|---|---|---|
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |

(56) References Cited

U.S. PATENT DOCUMENTS

| | | |
|---|---|---|
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H2037 H | 7/2002 | Yates et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,142 B1 | 10/2002 | Faller et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |

(56) References Cited

U.S. PATENT DOCUMENTS

| | | |
|---|---|---|
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nero |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |

(56) References Cited

U.S. PATENT DOCUMENTS

| | | |
|---|---|---|
| 7,147,638 B2 | 12/2006 | Chapman et al. |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,450,998 B2 | 11/2008 | Zilberman et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,506,791 B2 | 3/2009 | Omaits et al. |
| 7,510,107 B2 | 3/2009 | Timm et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,611,512 B2 | 11/2009 | Ein-Gal |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,717,915 B2 | 5/2010 | Miyazawa |

(56) References Cited

U.S. PATENT DOCUMENTS

| | | |
|---|---|---|
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,871,392 B2 | 1/2011 | Sartor |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,868 B2 | 5/2011 | Cooper |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,284 B2 | 8/2012 | Dycus et al. |
| 8,241,312 B2 | 8/2012 | Messerly |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,761 B2 | 12/2012 | Widenhouse et al. |

(56) References Cited

U.S. PATENT DOCUMENTS

| | | |
|---|---|---|
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,394,094 B2 | 3/2013 | Edwards et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,591,506 B2 | 11/2013 | Wham et al. |
| D695,407 S | 12/2013 | Price et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,876,858 B2 | 11/2014 | Braun |
| 8,882,766 B2 | 11/2014 | Couture et al. |
| 8,882,791 B2 | 11/2014 | Stulen |

(56) References Cited

U.S. PATENT DOCUMENTS

| | | |
|---|---|---|
| 8,888,776 B2 | 11/2014 | Dietz et al. |
| 8,888,783 B2 | 11/2014 | Young |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,308 B2 | 3/2015 | Horner et al. |
| 8,968,332 B2 | 3/2015 | Farritor et al. |
| 8,978,845 B2 | 3/2015 | Kim |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,731 B2 | 5/2015 | Joseph |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,101,385 B2 | 8/2015 | Shelton, IV et al. |
| 9,107,672 B2 | 8/2015 | Tetzlaff et al. |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,900 B2 | 5/2016 | Wu et al. |
| 9,351,754 B2 | 5/2016 | Vakharia et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,627,120 B2 | 4/2017 | Scott et al. |
| 9,642,669 B2 | 5/2017 | Takashino et al. |
| 9,649,111 B2 | 5/2017 | Shelton, IV et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,030 B2 | 7/2017 | Davison et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,757,142 B2 | 9/2017 | Shimizu |

(56) References Cited

U.S. PATENT DOCUMENTS

| | | |
|---|---|---|
| 9,757,186 B2 | 9/2017 | Boudreaux et al. |
| 9,782,214 B2 | 10/2017 | Houser et al. |
| 9,795,436 B2 | 10/2017 | Yates et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0212069 A1* | 9/2006 | Shelton ............... A61B 17/072 606/205 |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0234709 A1 | 9/2008 | Houser |

(56) References Cited

U.S. PATENT DOCUMENTS

| | | |
|---|---|---|
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143806 A1 | 6/2009 | Witt et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0270853 A1 | 10/2009 | Yachi et al. |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0222752 A1 | 9/2010 | Collins, Jr. et al. |
| 2010/0274278 A1 | 10/2010 | Fleenor et al. |
| 2010/0298743 A1 | 11/2010 | Nield et al. |
| 2011/0087220 A1 | 4/2011 | Felder et al. |
| 2011/0087224 A1 | 4/2011 | Cadeddu et al. |
| 2011/0230875 A1* | 9/2011 | Walberg .......... A61B 17/29 606/33 |
| 2011/0257680 A1 | 10/2011 | Reschke et al. |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0123783 A1* | 5/2013 | Marczyk .......... A61B 17/29 606/45 |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0194874 A1 | 7/2014 | Dietz et al. |
| 2014/0194875 A1 | 7/2014 | Reschke et al. |
| 2014/0257284 A1 | 9/2014 | Artale |
| 2014/0263539 A1* | 9/2014 | Leimbach ........ A61B 17/07207 227/175.1 |
| 2014/0330271 A1 | 11/2014 | Dietz et al. |
| 2015/0032150 A1 | 1/2015 | Ishida et al. |
| 2015/0080876 A1 | 3/2015 | Worrell et al. |
| 2015/0137422 A1 | 5/2015 | Horner et al. |
| 2015/0209103 A1 | 7/2015 | Artale et al. |
| 2015/0230853 A1 | 8/2015 | Johnson et al. |
| 2015/0230861 A1 | 8/2015 | Woloszko et al. |
| 2015/0250531 A1 | 9/2015 | Dycus et al. |
| 2015/0272602 A1 | 10/2015 | Boudreaux et al. |
| 2015/0272659 A1 | 10/2015 | Boudreaux et al. |
| 2015/0272660 A1 | 10/2015 | Boudreaux et al. |
| 2015/0305796 A1 | 10/2015 | Wang |
| 2015/0327918 A1 | 11/2015 | Sobajima et al. |
| 2015/0374430 A1 | 12/2015 | Weiler et al. |
| 2016/0008023 A1 | 1/2016 | Yates et al. |
| 2016/0038225 A1 | 2/2016 | Couture et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0066980 A1 | 3/2016 | Schall et al. |
| 2016/0074099 A1 | 3/2016 | Kappus et al. |
| 2016/0074108 A1 | 3/2016 | Woodruff et al. |
| 2016/0128762 A1 | 5/2016 | Harris et al. |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2017/0056097 A1 | 3/2017 | Monson et al. |
| 2017/0105787 A1 | 4/2017 | Witt et al. |
| 2017/0105789 A1 | 4/2017 | Boudreaux et al. |
| 2017/0189102 A1 | 7/2017 | Hibner et al. |
| 2017/0312014 A1 | 11/2017 | Strobl et al. |
| 2017/0312015 A1 | 11/2017 | Worrell et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325878 A1 | 11/2017 | Messerly et al. |
| 2017/0367751 A1 | 12/2017 | Ruddenklau et al. |
| 2018/0085156 A1 | 3/2018 | Witt et al. |

FOREIGN PATENT DOCUMENTS

| | | |
|---|---|---|
| CN | 1694649 A | 11/2005 |
| CN | 1922563 A | 2/2007 |
| CN | 2868227 Y | 2/2007 |
| CN | 102834069 A | 12/2012 |
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0443256 A1 | 8/1991 |
| EP | 0456470 A1 | 11/1991 |
| EP | 0340803 B1 | 8/1993 |
| EP | 0630612 A1 | 12/1994 |
| EP | 0482195 B1 | 1/1996 |
| EP | 0705571 A1 | 4/1996 |
| EP | 0612570 B1 | 6/1997 |
| EP | 0557806 B1 | 5/1998 |
| EP | 0640317 B1 | 9/1999 |
| EP | 0908148 B1 | 1/2002 |
| EP | 0722696 B1 | 12/2002 |
| EP | 1199044 B1 | 12/2005 |
| EP | 1293172 B1 | 4/2006 |
| EP | 0875209 B1 | 5/2006 |
| EP | 1704824 A1 | 9/2006 |

(56) References Cited

FOREIGN PATENT DOCUMENTS

| | | |
|---|---|---|
| EP | 1738795 A1 | 1/2007 |
| EP | 1749479 A1 | 2/2007 |
| EP | 1767157 A1 | 3/2007 |
| EP | 1254637 B1 | 8/2007 |
| EP | 1813201 A1 | 8/2007 |
| EP | 1844720 A1 | 10/2007 |
| EP | 1862133 A1 | 12/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1974771 A1 | 10/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 2090239 B1 | 7/2011 |
| EP | 1728475 B1 | 8/2011 |
| EP | 2353518 A1 | 8/2011 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 2508143 B1 | 2/2014 |
| GB | 2032221 A | 4/1980 |
| GB | 2472216 A | 2/2011 |
| GB | 2447767 B | 8/2011 |
| JP | H08229050 A | 9/1996 |
| JP | 2002186627 A | 7/2002 |
| JP | 2008018226 A | 1/2008 |
| JP | 5714508 B2 | 5/2015 |
| WO | WO-8103272 A1 | 11/1981 |
| WO | WO-9222259 A2 | 12/1992 |
| WO | WO-9307817 A1 | 4/1993 |
| WO | WO-9314708 A1 | 8/1993 |
| WO | WO-9322973 A1 | 11/1993 |
| WO | WO-9510978 A1 | 4/1995 |
| WO | WO-9635382 A1 | 11/1996 |
| WO | WO-9710764 A1 | 3/1997 |
| WO | WO-9800069 A1 | 1/1998 |
| WO | WO-9837815 A1 | 9/1998 |
| WO | WO-9840020 A1 | 9/1998 |
| WO | WO-9857588 A1 | 12/1998 |
| WO | WO-9923960 A1 | 5/1999 |
| WO | WO-9940857 A1 | 8/1999 |
| WO | WO-9940861 A1 | 8/1999 |
| WO | WO-9947058 A2 | 9/1999 |
| WO | WO-0024330 A1 | 5/2000 |
| WO | WO-0024331 A1 | 5/2000 |
| WO | WO-0025691 A1 | 5/2000 |
| WO | WO-0128444 A1 | 4/2001 |
| WO | WO-0154590 A1 | 8/2001 |
| WO | WO-0195817 A1 | 12/2001 |
| WO | WO-02062241 A1 | 8/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-2004011037 A2 | 2/2004 |
| WO | WO-2004032754 A2 | 4/2004 |
| WO | WO-2004032762 A1 | 4/2004 |
| WO | WO-2004032763 A2 | 4/2004 |
| WO | WO-2004078051 A2 | 9/2004 |
| WO | WO-2004084709 A2 | 10/2004 |
| WO | WO-2004112618 A2 | 12/2004 |
| WO | WO-2005002415 A2 | 1/2005 |
| WO | WO-2005009211 A2 | 2/2005 |
| WO | WO-2005052959 A2 | 6/2005 |
| WO | WO-2005122917 A1 | 12/2005 |
| WO | WO-2006021269 A1 | 3/2006 |
| WO | WO-2006036706 A1 | 4/2006 |
| WO | WO-2006042210 A2 | 4/2006 |
| WO | WO-2006055166 A2 | 5/2006 |
| WO | WO-2006119139 A2 | 11/2006 |
| WO | WO-2006129465 A1 | 12/2006 |
| WO | WO-2007047531 A2 | 4/2007 |
| WO | WO-2007063550 A2 | 6/2007 |
| WO | WO-2007130382 A2 | 11/2007 |
| WO | WO-2007143665 A2 | 12/2007 |
| WO | WO-2008020964 A2 | 2/2008 |
| WO | WO-2008031025 A2 | 3/2008 |
| WO | WO-2008035089 A1 | 3/2008 |
| WO | WO-2008045348 A2 | 4/2008 |
| WO | WO-2008099529 A1 | 8/2008 |
| WO | WO-2008101356 A1 | 8/2008 |
| WO | WO-2008130793 A1 | 10/2008 |
| WO | WO-2009018406 A2 | 2/2009 |
| WO | WO-2009022614 A1 | 2/2009 |
| WO | WO-2009027065 A1 | 3/2009 |
| WO | WO-2009036818 A1 | 3/2009 |
| WO | WO-2009039179 A1 | 3/2009 |
| WO | WO-2009059741 A1 | 5/2009 |
| WO | WO-2009067649 A2 | 5/2009 |
| WO | WO-2009082477 A2 | 7/2009 |
| WO | WO-2009149234 A1 | 12/2009 |
| WO | WO-2010017266 A1 | 2/2010 |
| WO | WO-2010056716 A2 | 5/2010 |
| WO | WO-2010083480 A2 | 7/2010 |
| WO | WO-2010104755 A1 | 9/2010 |
| WO | WO-2011008672 A2 | 1/2011 |
| WO | WO-2011044343 A2 | 4/2011 |
| WO | WO-2011044468 A2 | 4/2011 |
| WO | WO-2011044471 A2 | 4/2011 |
| WO | WO-2011084768 A1 | 7/2011 |
| WO | WO-2011089717 A1 | 7/2011 |
| WO | WO-2011144911 A1 | 11/2011 |
| WO | WO-2011146691 A2 | 11/2011 |
| WO | WO-2011146698 A2 | 11/2011 |
| WO | WO-2011146709 A2 | 11/2011 |
| WO | WO-2012044606 A2 | 4/2012 |
| WO | WO-2012166510 A1 | 12/2012 |
| WO | WO-2013034629 A1 | 3/2013 |
| WO | WO-2013062978 A2 | 5/2013 |
| WO | WO-2013102602 A2 | 7/2013 |
| WO | WO-2013131823 A1 | 9/2013 |
| WO | WO-2013154157 A1 | 10/2013 |
| WO | WO-2015017989 A1 | 2/2015 |
| WO | WO-2015017995 A1 | 2/2015 |
| WO | WO-2015197395 A8 | 12/2015 |

OTHER PUBLICATIONS

Cadeddu et al., "Magnetic positioning system for trocarless laparoscopic instruments," American College of Surgeons Poster, 2004.

Cadeddu et al., "Novel magnetically guided intra-abdominal camera to facilitate laparoendoscopic single site surgery: initial human experience," Surgical Endoscopy, SAGES Oral Manuscript, 2009.

Cadeddu et al., "Transabdominal magnetic anchoring system for trocar-less laparoscopic surgery," American Urological Association Poster, 2002.

Cadeddu et al., "Transabdominal magnetic anchoring system for trocar-less laparoscopic surgery," Journal of Urology Abstract, 2002.

(56) References Cited

OTHER PUBLICATIONS

Castellvi et al., "Completely transvaginal NOTES cholecystectomy in a porcine model using novel endoscopic instrumentation," Accepted for Poster Presentation, SAGES Annual Meeting, 2009.

Castellvi et al., "Hybrid transgastric NOTES cholecystectomy in a porcine model using a magnetically anchored cautery and novel instrumentation," Submitted for Presentation, ASGE, 2009.

Castellvi et al., "Hybrid transvaginal NOTES sleeve gastrectomy in a porcine model using a magnetically anchored camera and novel instrumentation," Accepted for Poster Presentation, SAGES Annual Meeting, 2009.

Duchene et al., "Magnetic positioning system for trocarless laparoscopic instruments," Engineering and Urology Society Poster, 2004.

Fernandez et al., "Development of a transabdominal anchoring system for trocar-less laparoscopic surgery," ASME Proceedings of/MECE, 2003.

Gedeon et al., "Maximizing coupling strength of magnetically anchored notes instruments: How thick can we go?" Submittedfor Presentation, Poster, SAGES Annual Meeting, 2008.

Gedeon et al., "Maximizing coupling strength of magnetically anchored notes instruments: How thick can we go?" SAGES Annual Meeting Poster, 2008.

Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.

Peirs et al., "A miniature manipulator for integration in self-propelling endoscope," Sensors and Actuators, 92:343-9, 2001.

Raman et al., "Complete transvaginal NOTES nephrectomy using magnetically anchored instrumentation," Journal of Endourology, 23(3):, 2009.367-371,2009.

Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.

Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.

Scott et al., "Completely transvaginal NOTES cholecystectomy using magnetically anchored instruments," Surg. Endosc., 21:2308-2316, 2007.

Scott et al., "Evaluation of a novel air seal access port for transvaginal notes cholecystectomy," Submitted for Presentation, SAGES Annual Meeting, 2008.

Scott et al., "Magnetically anchored instruments for transgastric endoscopic surgery," Oral Presentation for SAGES Annual Meeting, Emerging Technology Oral Abstract ET005, 2006.

Scott et al., "Optimizing magnetically anchored camera, light source, graspers, and cautery dissector for transvaginal notes cholecystectomy," Submitted for Presentation, SAGES Annual Meeting, 2008.

Scott et al., "Short-term survival outcomes following transvaginal NOTES cholecystectomy using magnetically anchored instruments," Oral Presentation, ASGE Annual Meeting/DDW, 2007.

Scott et al., "Trans gastric, transcolonic, and transvaginal cholecystectomy using magnetically anchored instruments," SAGES Annual Meeting Poster, 2007.

Scott et al., "Transvaginal NOTES cholecystectomy using magnetically anchored instruments," Abstract for Video Submission, ASGE II1h Annual Video Forum, 2007.

Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.

Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.

Swain et al., "Wireless endosurgery for NOTES," Digestive Disease Week (DDW), American Society for Gastrointestinal Endoscopy (ASGE) Annual Meeting Abstract, 2008.

Tang et al., "Live video manipulator for endoscopy and natural orifice transluminal endoscopic surgery (with videos)," Gastrointestinal Endoscopy, 68:559-564, 2008.

Zeltser et al., "Single trocar laparoscopic nephrectomy using magnetic anchoring and guidance system in the porcine model," The Journal of Urology, 178:288-291, 2007.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Covidien Brochure, [Value Analysis Brief], LigaSure Advance™ Pistol Grip, dated Rev. Apr. 2010 (7 pages).

(56) References Cited

OTHER PUBLICATIONS

Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Glaser and Subak-Sharpe,Integrated Circuit Engineering, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al., "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Leonard I. Malis, M.D., "The Value of Irrigation During Bipolar Coagulation," 1989.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http///wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hömann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

\* cited by examiner

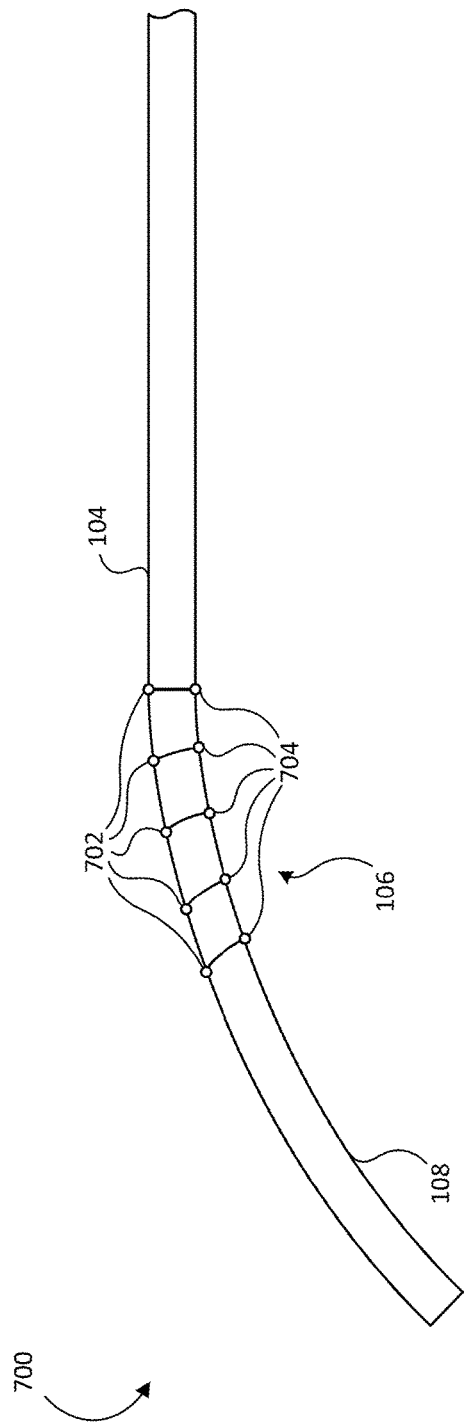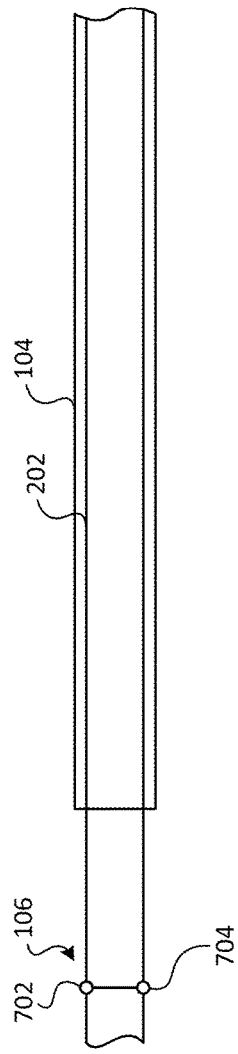
FIG. 7A
FIG. 7B

ARTICULATING RADIO FREQUENCY (RF) TISSUE SEAL WITH ARTICULATING STATE SENSING

The present disclosure is related generally to surgical devices. In particular, the present disclosure is related to surgical devices with various mechanisms for controlling articulation of an end effector on the distal end of a shaft assembly.

BACKGROUND

Endoscopy refers to looking inside a human body for medical reasons using an instrument called an endoscope. Endoscopy is a minimally invasive diagnostic medical procedure used to evaluate interior surfaces of an organ or other tissue by inserting a small tube into the body, often, but not necessarily, through a natural body opening of a patient or through a relatively small incision. Using the endoscope, a surgeon may view surface conditions of the organs or other tissue, including abnormal or diseased tissue such as lesions and other various surface conditions. The endoscope may have a rigid or a flexible tube and, in addition to providing an image for visual inspection and photography, the endoscope may be adapted and configured for taking biopsies, retrieving foreign objects, and introducing medical instruments to a tissue treatment region, referred to generally herein as a surgical site.

Laparoscopic surgery is a minimally invasive surgical technique in which operations are performed through small incisions (usually 0.5 cm to 1.5 cm) or keyholes, as compared to the larger incisions required in traditional open-type surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

Various other kinds of surgery may be performed through small incisions or other natural orifices. For example, sealing tissue of a lumen wall may be achieved by applying electrosurgical energy to a lumen wall through use of electrosurgical jaws attached to a thin, long shaft of a surgical device. In other cases, injections may be applied to tissue within a small incision through a trocar attached to the long shaft of a surgical device. However, the small incision or opening may cause a lack of visibility into the surgical site. It may be desirable to provide various mechanisms for controlling and monitoring the medical instruments inserted through the small incisions or openings when performing surgery on a patient.

SUMMARY

In some embodiments, a surgical instrument is provided.

1. In one example, a surgical instrument comprises a handle assembly; a shaft assembly coupled to a distal end of the handle assembly; an end effector comprising a surgical tool configured to interface with tissue of a patient; an articulation joint coupled to the shaft assembly and the end effector and configured to articulate the end effector such that the end effector can be oriented at a different angle relative to the shaft assembly, the articulation joint comprising a first maximum articulation angle in a first direction such that the end effector is prevented from articulating beyond the first maximum articulation angle in the first direction, and a second maximum articulation angle in a second direction such that the end effector is prevented from articulating beyond the second maximum articulation angle in the second direction; and an articulation control mechanism operatively coupled to the articulation joint through the shaft assembly and configured to: control movement of the articulation joint between the first maximum articulation angle and the second maximum articulation angle; determine that the articulation joint has articulated to the first maximum articulation angle; provide a first indication that the articulation joint has articulated to the first maximum articulation angle; determine that the articulation joint has articulated to the second maximum articulation angle; and provide a second indication that the articulation joint has articulated to the second maximum articulation angle.

2. The surgical instrument of example 1, wherein: the shaft assembly comprises a guiding mechanism operatively coupled to the articulation joint and configured to manipulate the articulation joint; and the articulation control mechanism comprises: a latch coupled to the guiding mechanism; a motor operatively coupled to the latch and configured to drive the latch along a longitudinal axis parallel to the shaft assembly; and a switch coupled to the motor comprising a first and second button and both configured to operate the motor.

3. The surgical instrument of example 1 or 2, wherein: the first button is configured to direct the motor to drive the latch in a first direction along the longitudinal axis distally away from the handle assembly; and the second button is configured to direct the motor to drive the latch in a second direction along the longitudinal axis proximally toward the handle assembly.

4. The surgical instrument of example 3, wherein: the latch comprises a raised end positioned toward the switch; and the switch comprises: a first prominent end positioned at a first edge of the switch near the first button and facing toward the latch; and a second prominent end positioned at a second edge of the switch near the second button and facing toward the latch.

5. The surgical instrument of example 4, wherein: the articulation joint reaches the first maximum articulation angle when the raised end of the latch touches the first prominent end of the switch; and the articulation joint reaches the second maximum articulation angle when the raised end of the latch touches the second prominent end of the switch.

6. The surgical instrument of any one of examples 1-5, further comprising: a first home position switch coupled to the shaft assembly and positioned distal to the handle assembly, the first home position switch disposed to be pressed into the shaft assembly; and a second home position switch coupled to the shaft assembly and positioned distal to the handle assembly, the second home position switch disposed to be pressed into the shaft assembly; wherein the articulation joint is positioned distal to both the first home position switch and the second home position switch.

7. The surgical instrument of example 6, wherein the first home position switch pressed into the shaft assembly simultaneously with the second home position switch pressed into the shaft assembly causes the articulation joint to be articulated to an angle parallel to the shaft assembly.

8. The surgical instrument of any one of examples 1-7, wherein the articulation joint comprises: a first link and a second link, the first and second links coupled together by way of a hinge; a first sensor coupled to a first edge of the first link; and a second sensor coupled to a second edge of the first link, the second edge located opposite of the hinge.

9. The surgical instrument of example 8, wherein articulation of the articulation joint in the first direction causes the first sensor to touch the second link, and articulation of the articulation joint in the second direction causes the second sensor to touch the second link.

10. The surgical instrument of any one of examples 1-9, further comprising a rotation knob coupled to the shaft assembly and configured to rotate the shaft assembly, wherein rotation of the shaft assembly causes rotation of the articulation joint.

11. The surgical instrument of example 10, wherein the shaft assembly comprises an orientation mechanism configured to maintain orientation of the articulation joint by the articulation control mechanism such that the articulation control mechanism causes the articulation joint to articulate, wherein relative to a first rotation reference point of 0-180 degrees, pressing a first button provides an articulation in a first direction and pressing a second button provides an articulation in a second direction, and wherein relative to a second reference point of 181-360 degrees pressing the first button provides an articulation in the second direction and pressing the second button provides articulation in the first direction.

12. The surgical instrument of example 11, wherein the orientation mechanism comprises a commutator ring coupled to the shaft assembly and operatively coupled to the articulation control mechanism, such that relative to the first rotation reference point of 0-180 degrees, pressing the first button provides an articulation in the first direction and pressing the second button provides an articulation in the second direction, and wherein relative to the second reference point of 181-360 degrees pressing the first button provides an articulation in the second direction and pressing the second button provides articulation in the first direction.

13. In another example, a surgical instrument comprises a handle assembly; a shaft assembly coupled to a distal end of the handle assembly; an end effector comprising a surgical tool configured to interface with tissue of a patient; an articulation joint coupled to the shaft assembly and the end effector and configured to articulate the end effector such that the end effector can be oriented at a different angle relative to the shaft assembly, the articulation joint comprising a first maximum articulation angle in a first direction such that the end effector is prevented from articulating beyond the first maximum articulation angle in the first direction, and a second maximum articulation angle in a second direction such that the end effector is prevented from articulating beyond the second maximum articulation angle in the second direction; and an articulation control mechanism operatively coupled to the articulation joint through the shaft assembly and configured to: control movement of the articulation joint between the first maximum articulation angle and the second maximum articulation angle; determine that the articulation joint has articulated to the first maximum articulation angle; provide a first indication that the articulation joint has articulated to the first maximum articulation angle; determine that the articulation joint has articulated to the second maximum articulation angle; and provide a second indication that the articulation joint has articulated to the second maximum articulation angle; wherein the shaft assembly comprises a guiding mechanism operatively coupled to the articulation joint and configured to manipulate the articulation joint; and the articulation control mechanism comprises: a latch coupled to the guiding mechanism; and a wheel coupled to the latch and configured to rotate along a wheel axis; wherein the latch is configured to move the guiding mechanism along a longitudinal axis of the shaft assembly by a rotation of the wheel.

14. The surgical instrument of example 13, wherein the articulation control mechanism further comprises: a raised ridge coupled to the wheel; a circular housing coupled to the wheel and disposed on the outside of the surgical instrument such that the circular housing at least partially covers the wheel; a switch coupled to the circular housing and comprising a first button and a second button configured to direct rotation of the wheel; and a motor operatively coupled to the first button, the second button, and the wheel and configured to cause rotation of the wheel upon operation of the first or the second button.

15. The surgical instrument of example 14, wherein: the circular housing comprises an opening that partially exposes the wheel and exposes the raised ridge, the opening having a first edge and a second edge; the rotation of the wheel causes rotation of the raised ridge; the articulation joint reaches the first maximum articulation angle when rotation of the wheel causes the raised ridge to touch the first edge of the opening of the circular housing; and the articulation joint reaches the second maximum articulation angle when rotation of the wheel causes the raised ridge to touch the second edge of the opening of the circular housing.

16. The surgical instrument of any one of examples 13-15, wherein the articulation control mechanism further comprises: a first and a second sensor, both coupled to the handle assembly, the first and the second sensors positioned on opposite sides of the latch equidistant to a central position of the latch, wherein the latch positioned at the central position indicates the articulation joint is angled parallel to the shaft assembly; a knob coupled to the wheel and configured to rotate the wheel along the wheel axis; and a proximity sensor operatively coupled to the wheel and configured to measure a first distance to the first sensor and measure a second distance to the second sensor.

17. The surgical instrument of example 16, wherein: the rotation of the knob causes rotation of the proximity sensor; the articulation joint reaches the first maximum articulation angle when the proximity sensor is rotated to be closest in distance to the first sensor; and the articulation joint reaches the second maximum articulation angle when the proximity sensor is rotated to be closest in distance to the second sensor.

18. In another example, a surgical instrument comprises a handle assembly; a shaft assembly coupled to a distal end of the handle assembly; an end effector comprising a surgical tool configured to interface with tissue of a patient; an articulation joint coupled to the shaft assembly and the end effector and configured to articulate the end effector such that the end effector can be oriented at a different angle relative to the shaft assembly; a first home position switch coupled to the shaft assembly and positioned distal to the handle assembly, the first home position switch disposed to be pressed into the shaft assembly; and a second home position switch coupled to the shaft assembly and positioned distal to the handle assembly, the second home position switch disposed to be pressed into the shaft assembly; wherein the articulation joint is positioned distal to both the first home position switch and the second home position switch.

19. The surgical instrument of example 18, wherein the first home position switch pressed into the shaft assembly simultaneously with the second home position switch pressed into the shaft assembly causes the articulation joint to be articulated to an angle parallel to the shaft assembly.

20. The surgical instrument of example 18, wherein the articulation joint comprises: a first link and a second link, the first and second links coupled together by way of a hinge; a first sensor coupled to a first edge of the first link; and a second sensor coupled to a second edge of the first link, the second edge located opposite of the hinge.

21. The surgical instrument of example 20, wherein articulation of the articulation joint in the first direction causes the first sensor to touch the second link, and articulation of the articulation joint in the second direction causes the second sensor to touch the second link.

22. The surgical instrument of any one examples 18-21, wherein the end effector comprises a trocar.

23. The surgical instrument of any one of examples 18-22, wherein the end effector comprises a pair of electrosurgical jaws configured to seal tissue using electrosurgical energy.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 3A illustrates an overhead view of the internal structure of the motorized articulation switch shown in FIG. 2;

FIG. 3B illustrates an example of the switch in a state after a user presses on the switch at a first impression when the latch is positioned over the pivot point at hinge;

FIG. 3C illustrates an example of the motorized articulation assembly reaching a maximum movement of the articulation in one direction after the switch has been pressed in the direction marked "A" at the first impression 208 as shown in FIG. 3B;

FIG. 3D illustrates an example of the switch in a state after a user presses on the switch at a second impression when the latch is positioned over the pivot point at hinge; and FIG. 3E illustrates an example of the motorized articulation assembly reaching a maximum movement of the articulation in the other direction.

FIG. 7A is an illustration providing an example mechanism for determining when the articulation joint is articulated, according to some embodiments.

FIG. 7B shows another variation where the shaft assembly is housing the rod or shaft, according to some embodiments.

DESCRIPTION

Figure 1:
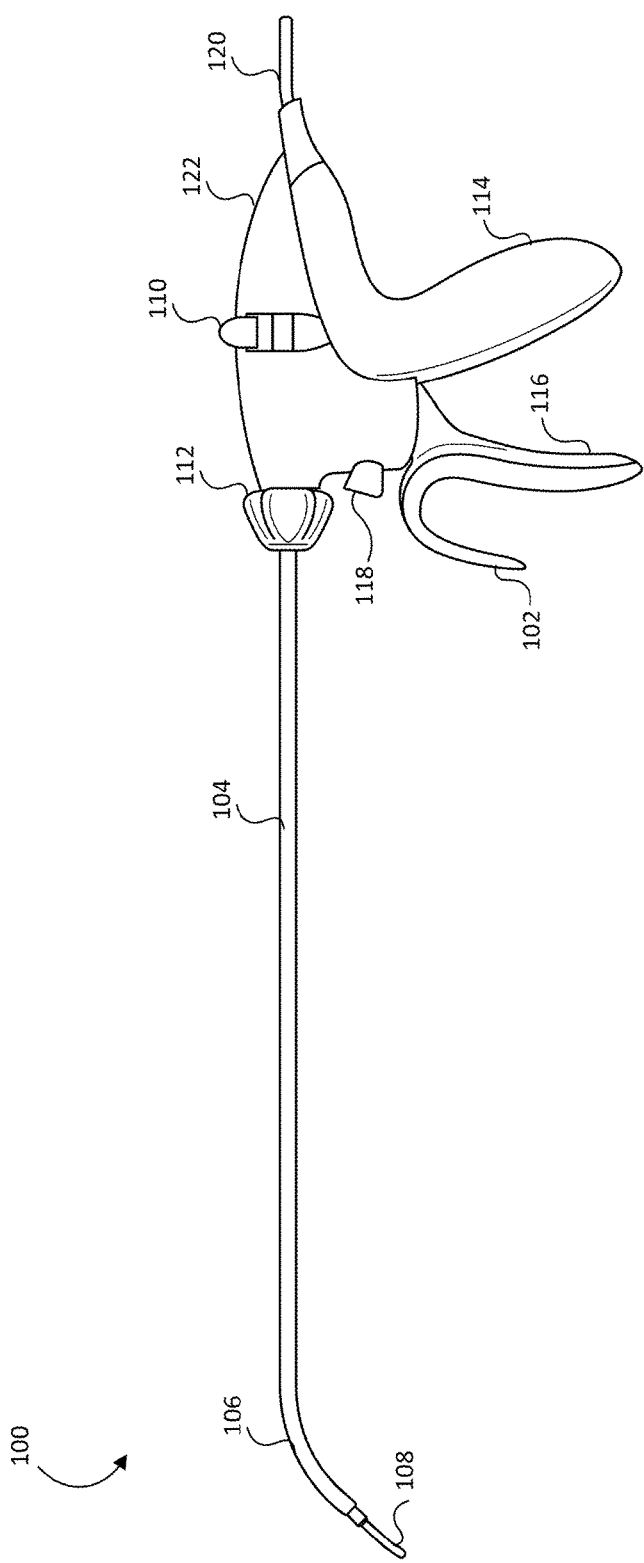
FIG. 1 is an illustration of a surgical instrument comprising a trigger assembly, a shaft assembly, an articulation joint, and an end effector according to some embodiments.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Methods and apparatuses are presented for improved mechanics in devices with articulating end effectors. Surgeons and other users of medical devices with articulating arms or shafts may perform various types of surgery involving inserting the articulating arm or shaft into a wound or incision of a patient. The distal end of the medical device may first enter the wound or incision with a straight distal end, and once inside the patient's body cavity, the medical device may be manipulated to articulate the distal end to perform various kinds of surgery at varying angles inside the patient. For example, a device with an articulating shaft may include a pair of electrosurgical jaws at the end effector and may be configured to seal tissue located at various angles inside a body cavity. As another example, a device with an articulating shaft may include a trocar at the distal end and may be configured to inject liquid through the needle of the trocar to a location angled from inside a surgical site.

However, the incision or opening into the surgical site may be sufficiently large only to allow insertion of the end effector and the shaft of the medical device. The surgeon or other user may therefore lack visibility of the end effector while in the surgical site. Problems and potential injuries may arise due to this lack of visibility, in particular when manipulating the end effector that is capable of articulating in various angles inside the surgical site. For example, if the medical device can articulate to different degrees, e.g., from centerline to 45° of center and anywhere in between, the user of the medical device may not be able to see how sharp of an angle the end effector has articulated while inside the surgical site, including whether the end effector has articulated to its maximum angle. As another example, the user may have trouble determining if the end effector is straight so as to allow the shaft to exit the opening having a straight end effector. It may be desirable therefore to include various mechanisms for aiding use of articulating distal ends of devices, particularly when line of sight of the articulating distal end is obscured.

To aid the user of a device with an articulating end when the user cannot see fully the position and orientation of the articulating distal end, in some embodiments, various mechanical and motorized devices are presented for indicating to the user when the distal and has reached its maximum articulation angle. In some embodiments, various mechanical and electrical devices are presented for automatically reverting the distal end to a straight position (sometimes referred to herein as a home position) when the user manually removes the medical device from inside a surgical site. In some embodiments, various mechanical and electrical devices are presented for determining whether the distal end is articulated, and in some cases may determine to what degree the distal end is articulated. In some embodiments, various mechanical and electrical devices are presented for ensuring that the user will articulate the distal end in the direction he intends, even when the distal end may be rotated 360°.

Referring to FIG. 1, a surgical instrument 100 is illustrated according to some embodiments, comprising a trigger assembly 102, a shaft assembly 104, an articulation joint 106, and an end effector 108. An articulation control knob 110 may control the articulation of the articulation joint 106 by way of articulation cables or bands operably coupled to the articulation control knob 110. A rotation knob 112 may be operably coupled to the shaft assembly 104 and may enable rotation of the shaft assembly 104 up to and including 360 degrees. The trigger assembly 102 may be configured to clamp and independently fire the end effector 108 coupled to the shaft assembly 104 of the surgical instrument 100. In some embodiments, the end effector 108 may include a pair of electrosurgical jaws for performing tissue sealing operations. In other cases, the end effector 108 may include a trocar or other type of needle. Other types of devices attached to the distal end of the shaft assembly 104 may be apparent to those with skill in the art, and embodiments not so limited.

Regardless of the type of tool is part of the end effector 108, the articulation joint 106 may allow the end effector 108 to angle in various directions while the main portion of the shaft assembly 104 remains straight. For example, in some embodiments, the articulation knob 110 may be rotated or turned to allow, via a series of articulation cables or bands, the articulation joint 106 to turn to the left or to the right up to some maximum angle, e.g., up to 90° from center. In combination with the rotation knob 112, which may allow the shaft assembly 104 to rotate along the long axis a full 360°, the end effector 108 may therefore be configured to be angled in a wide variety of directions, for example angled straight down, or angled straight up.

The surgical instrument 100 comprises a handle assembly 122. The shaft assembly 104 comprises a proximal end and a distal end. The proximal end of the shaft assembly 104 is coupled to the distal end of the handle assembly 122. The articulation control knob 108 and the rotation control knob 112 may be operatively coupled to the distal end of the handle assembly 122 and may be configured to receive and couple to the proximal end of shaft assembly 104. The end effector 108 may be coupled to the distal end of the shaft assembly 104. The handle assembly 122 may comprise a pistol grip 114. The handle assembly 122 may include a left handle housing shroud and a right handle housing shroud. The trigger assembly 102 may include a trigger 116 actuatable towards the pistol grip 114. The rotatable shaft knob 112 may be configured to rotate the shaft assembly 104 with respect to the handle assembly 122. In some embodiments, the handle assembly 122 may further comprise an energy button 118 configured to provide electrosurgical energy to one or more electrodes in the end effector 108.

In some embodiments, the shaft assembly 104 may include a closure/jaw actuator, a firing/cutting member actuator, and an outer sheath. In some embodiments, the outer sheath may include the closure actuator. The outer sheath may include one or more contact electrodes on a distal end configured to interface with the end effector 108. The one or more contact electrodes may be operatively coupled to the energy button 118 and an energy source, such as a source connected through power cable 120. In other cases, the shaft assembly 104 may include another type of medical tool suitable to be placed at the distal end, such as a trocar more other type of injection needle.

Figure 2:
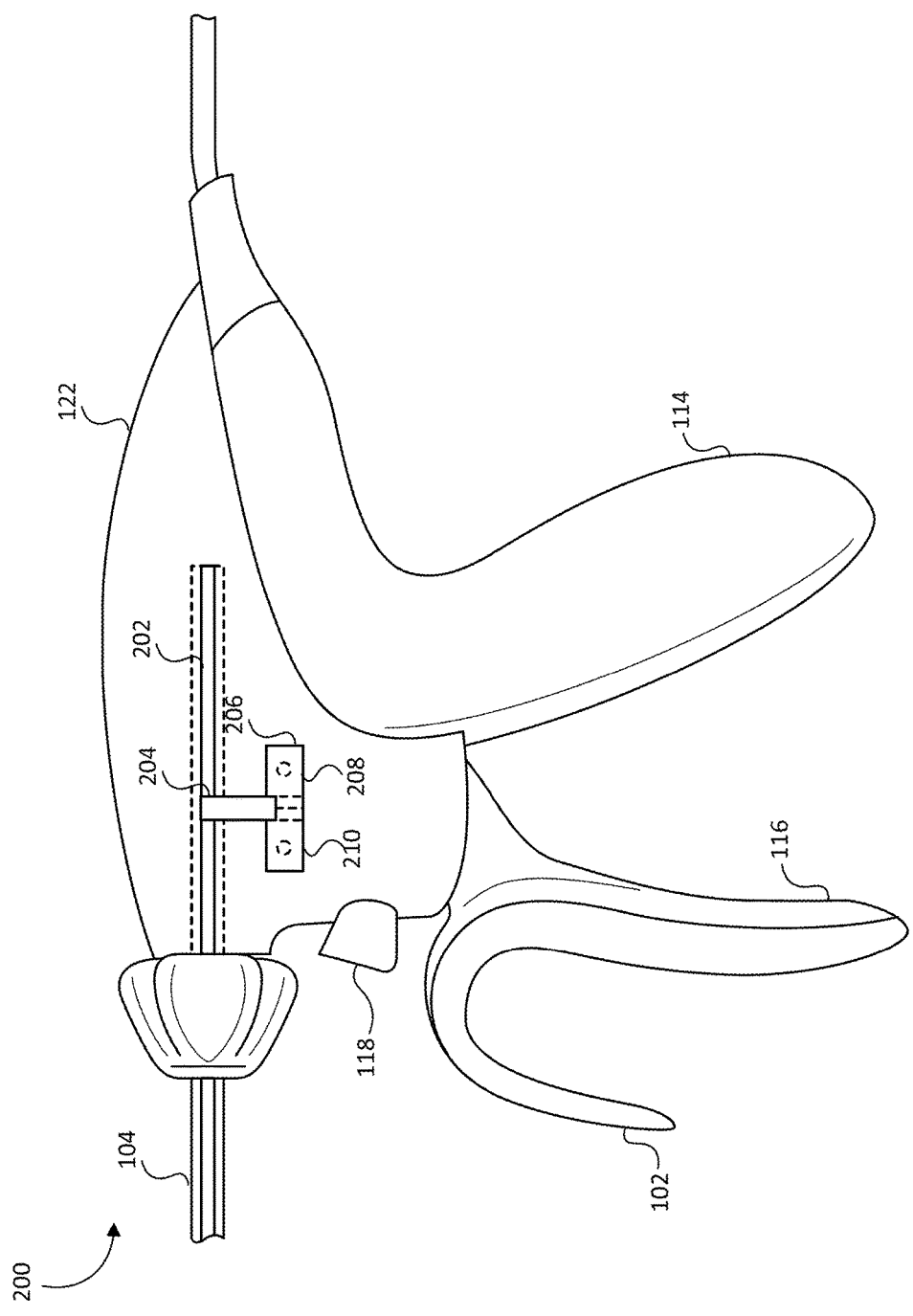
FIG. 2 is an illustration showing an example medical device with a motorized switch for articulating the end effector, according to some embodiments.

Referring to FIG. 2, illustration 200 shows an example medical device similar to medical instrument 100 (FIG. 1) with a motorized switch for articulating the end effector, according to some embodiments. When the end effector 108 (FIG. 1) at the distal end of the shaft assembly 104 is in a surgical site of the patient, the surgeon utilizing the medical device shown in illustration 200 may not be able to see the position and orientation of the articulating end effector 108. Moreover, the surgeon may therefore be unable to unambiguously determine if the articulation of the end effector has reached a maximum angle, versus if the end effector is simply stuck or jammed in the surgical site when attempting to articulate. The motorized switch mechanism as shown in illustration 200 may be able to address at least this issue, according to some embodiments.

Here, a rod or cable 202 used to guide or conduct the articulation of the end effector 108 (FIG. 1) at the articulation joint 106 (FIG. 1) may be coupled to a lever or latch 204. The latch 204 may be connected to a switch 206 that may be pressed by the surgeon to control the articulating movement. The switch 206 may be pressed at impressions 208 and 210, where pushing the switch 206 at impression 208 may drive a mechanical motor to drag the latch 204 in one direction, e.g., either distally or proximally along the longitudinal axis of the shaft assembly 104, depending on the implementation. In some embodiments, the movement of the latch 204 may correspondingly move the rod or cable 202, thereby causing articulation of the end effector 108. Similarly, the surgeon pressing on impression 210 may cause the latch 204 to move in the opposite direction from pressing on impression 208, thereby causing articulation of the end effector 108 in the opposite direction. In some embodiments, the motorized switch assembly discussed herein may be built to one side of the handle assembly 122, while in other cases the motorized switch assembly discussed herein may be built on the top of the handle assembly 122, and embodiments are not so limited.

In some embodiments, the motorized switch assembly described herein may be constructed in such a way so as to indicate to a user when the articulation has reached its maximum angle, in either direction. The latch 204 may be configured to move to one end of the switch 206 and may be physically prevented from moving beyond a particular threshold, the physical prevention coinciding with the maximum angle that the end effector 108 can articulate to. Similarly, the latch 204 may be configured to move to the other end of the switch 206 and may be physically prevented from moving beyond that threshold, coinciding with the maximum angle of the end effector 108 articulating to in the other direction.

In some cases, the medical device of illustration 200 may include a trigger assembly 102 and an energy button 118, like the medical instrument 100. These components may not be included in this illustration for clarity purposes, and embodiments are not so limited.

Referring to FIGS. 3A-3E, various internal views of an example of the motorized articulation switch described in FIG. 2 are shown. These internal views may illustrate one example of how the maximum angle of articulation may be determined and may be prevented from exceeding, according to some embodiments. For example, with reference now to FIG. 3A, starting at illustration 300, an overhead view of the internal structure of the motorized articulation switch of FIG. 2 is shown. Illustration 300 shows the motorized articulation switch in a neutral position, where the latch 204 is positioned in the center of the switch 206. As shown, the latch 204 is coupled to the cable or rod 202. As shown, the latch 204 may have a raised or prominent end sticking out beyond the cable or rod 202 close to the switch 206. Also as shown, the switch 206 may have two raised or prominent ends sticking out on both sides of the switch 206, close to the cable or rod 202. The rod 202, the latch 204, a portion of the switch 206, and a pivot hinge 212 coupled to the switch 206 and acting like a fulcrum for the switch 206 may be built inside the housing of a medical device, such as medical instrument 100 (FIG. 1). The impressions 208 and 210 may be located physically outside of the medical device housing, allowing the user to press on the switch 206 through the impressions 208 or 210. When the latch 204 is positioned over the pivot point at hinge 212, the switch 206 may be pressed at impression 208 to pivot the switch 206 counterclockwise about the hinge 212 in the direction marked "A" as shown below with reference to FIG. 3B or the switch 206 may be pressed at impression 210 to pivot the switch 206 clockwise about the hinge 212 in the direction marked "B" as shown below with reference to FIG. 3D.

Figure 3A:
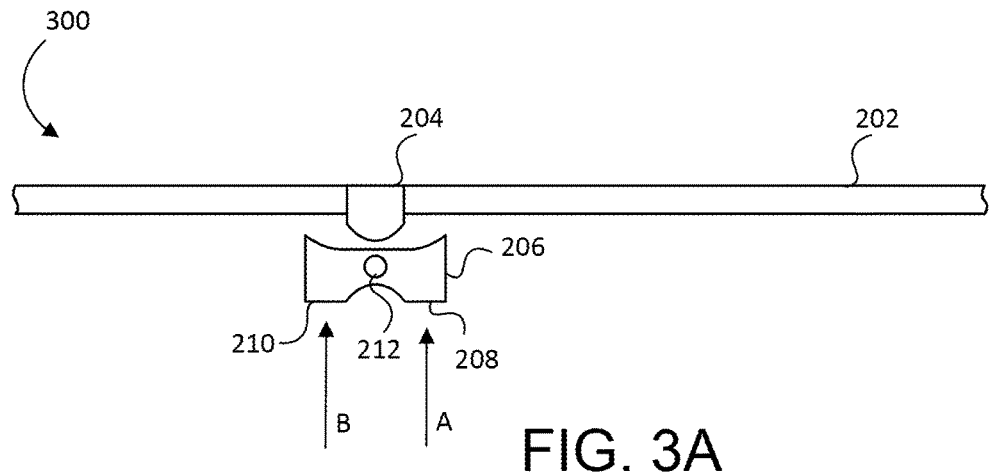
FIGS. 3A-3E illustrate an example of the motorized articulation assembly reaching a maximum movement of the articulation in one direction, according to some embodiments, where.
Figure 3B:
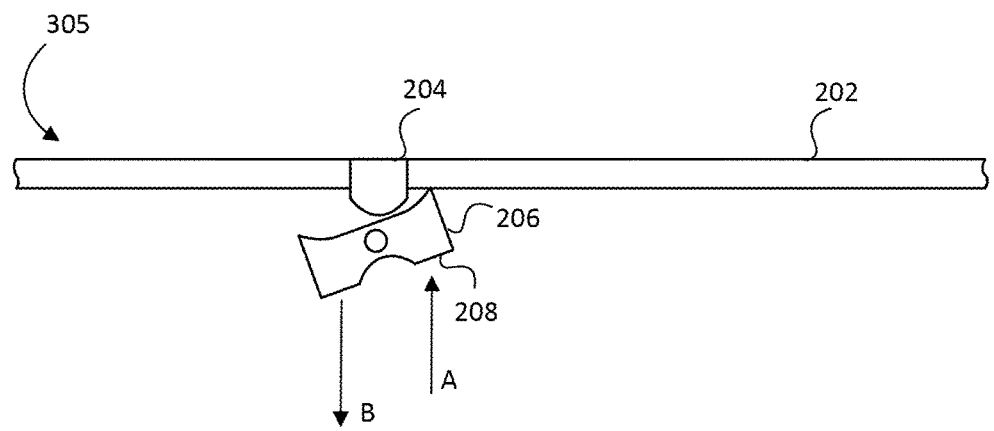

Referring now to FIG. 3B, illustration 305 shows an example of the switch 206 in a state after a user presses on the switch 206 at a first impression 208 when the latch 204 is positioned over the pivot point at hinge 212. Pressing the switch 206 at impression 208 causes the switch 206 to pivot about the hinge 212 in a counterclockwise direction such that the switch 206 at impression 208 moves in the direction marked "A," while the impression 210 may move in the direction marked "B." Here, when the user presses on the switch 206 at the impression 208, i.e., in the direction marked "A," in some embodiments, a motoring gear assembly coupled to the switch 206 may cause the cable or rod 202 to move to the right in the illustration 310, i.e., proximally toward the user, where the shaft assembly 104 would be located distally from the user and to the left in the illustration 310.

Figure 3C:
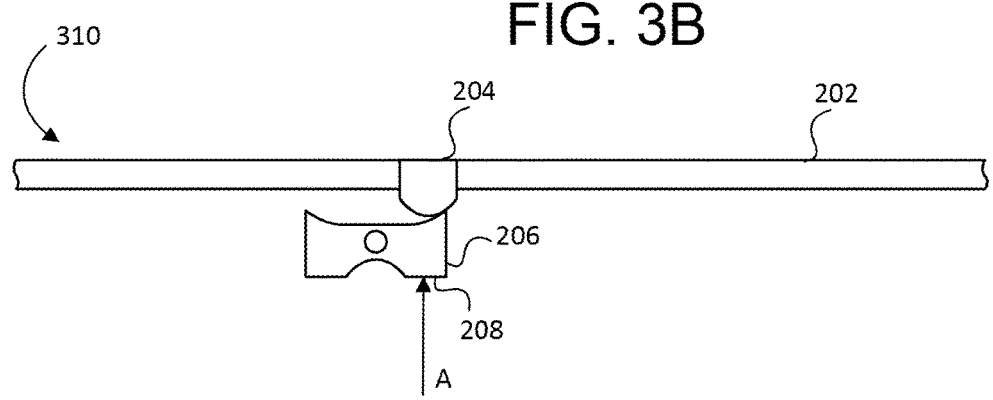

Referring now to FIG. 3C, illustration 310 shows an example of the motorized articulation assembly reaching a maximum movement of the articulation in one direction after the switch 206 has been pressed in the direction marked "A" at the first impression 208 as shown in FIG. 3B, according to some embodiments. Still with reference to FIG. 3C, in so doing, the latch 204 would correspondingly move toward the right, until the latch 204 touches the right prominent end of the switch 206 and would stop, unable to move any further to the right. In some embodiments, the latch 204 physically preventing the rod or cable 202 from moving further to the right due to the latch 204 being physically stopped by the prominent end of the switch 206 also may correspond to the articulation joint 106 (FIG. 1) reaching a maximum articulation angle. When the latch 204 is positioned over the prominent end of the switch 206, the switch cannot be rocked or pivoted when the user presses on the switch 206 at impression 208 in the direction marked "A," thus providing the user with a resistance or tactile feedback. With the latch 204 in the position shown in FIG. 3C, the user can press on the switch 206 at the second impression 210.

Figure 3D:
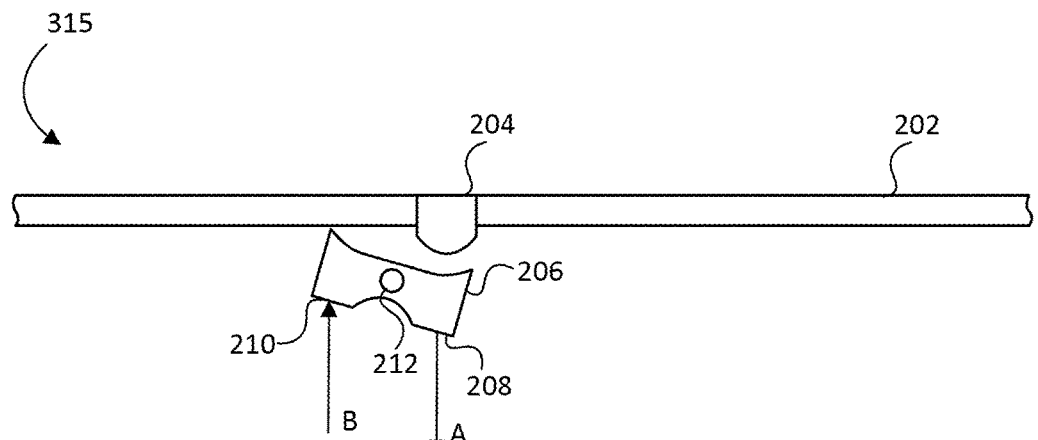

Referring now to FIG. 3D, illustration 315 shows an example of the switch 206 in a state after a user presses on the switch 206 at a second impression 210 when the latch 204 is positioned over the pivot point at hinge 212. Pressing the switch 206 at impression 210 causes the switch 206 to pivot about the hinge 212 in clockwise direction such that the switch 206 at impression 208 moves in the direction marked "A," while the impression 210 may move in the direction marked "B." Here, when the user presses on the switch 206 at the impression 210, i.e., in the direction marked "B," in some embodiments, the motoring gear assembly coupled to the switch 206 may cause the cable or rod 202 to move to the left in the illustration 320, i.e., distally away from the user. In so doing, the latch 204 would correspondingly move toward the left, until the latch 204 touches the other prominent end of the switch to a six and would stop, unable to move any further to the left. In some embodiments, the latch 204 physically preventing the rod or cable 202 from moving further to the left due to the latch 200 for being physically stopped by the prominent end of the switch 206 also may correspond to the articulation joint 106 reaching the other maximum articulation angle.

Figure 3E:
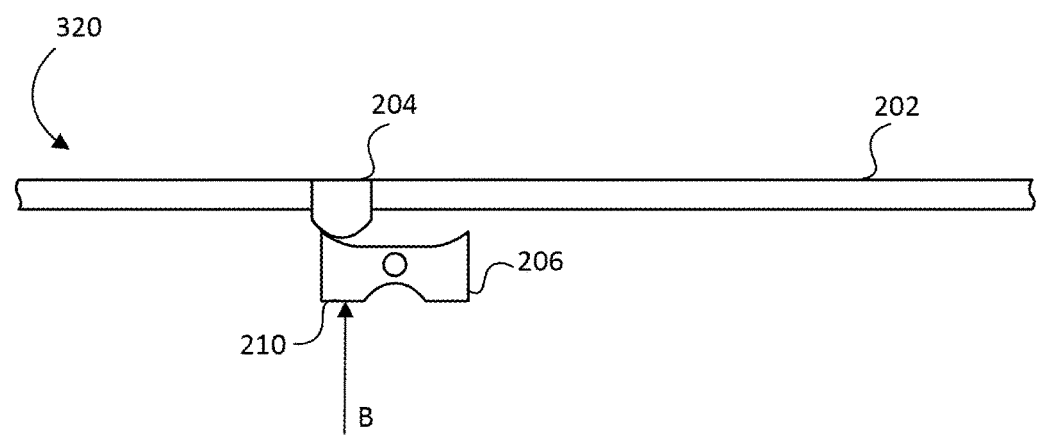

Referring now to FIG. 3E, illustration 320 shows an example of the motorized articulation assembly reaching a maximum movement of the articulation in the other direction, according to some embodiments. In so doing, the latch 204 would correspondingly move toward the left, until the latch 204 touches the left prominent end of the switch 206 and would stop, unable to move any further to the right. In some embodiments, the latch 204 physically preventing the rod or cable 202 from moving further to the right due to the latch 204 being physically stopped by the prominent end of the switch 206 also may correspond to the articulation joint 106 (FIG. 1) reaching a maximum articulation angle. When the latch 204 is positioned over the left prominent end of the switch 206, the switch 206 cannot be rocked or pivoted when the user presses on the switch at impression 210 in the direction marked "B," thus providing the user with a resistance or tactile feedback.

In this way, the position of the latch 204 may allow the user to tactilely and visually determine that the articulation joint 106 has reached a maximum articulation angle, e.g., fully articulating to the right or to the left (the actual maximum angle of which may vary according in different embodiments). In contrast, if the latch 204 had not reached the end of the switch 206, but the rod or cable 202 was still not moving, the user may determine that the maximum articulation angle had not been reached, and instead may conclude that some other problem has occurred. For example, it may be the case that the motor has died, or that the end effector 108 has hit a wall or barrier inside the surgical site and is physically unable to move further. Thus, the example motorized articulation assembly described in FIGS. 2 and 3A-3C may provide additional information for the user of the medical device while the user may have difficulty seeing inside the surgical site.

Figure 4A:
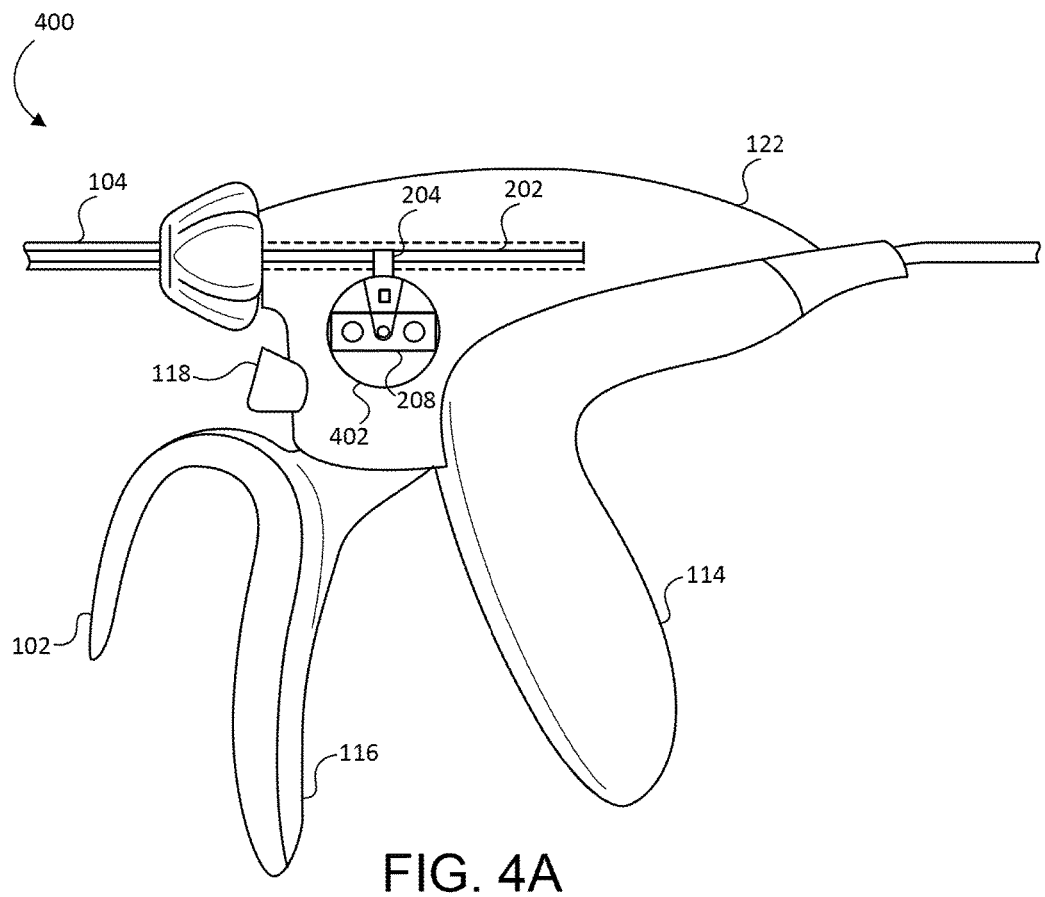
FIG. 4A is an illustration providing another example mechanism for aiding the user in determining when the maximum articulation angle of the articulation joint has been reached, according to some embodiments.

Referring to FIG. 4A, illustration 400 provides another example mechanism for aiding the user in determining when the maximum articulation angle of the articulation joint 106 (FIG. 1) has been reached, according to some embodiments. Here, an example handle assembly 122 may include a motorized switch and wheel assembly 402 configured to manipulate the articulation joint 106 and provide visual and tactile indicators for when the maximum articulation angles have been reached. In some embodiments, the motorized switch and wheel assembly 402 may be built into the side of the handle assembly 122, as shown, while in other cases the motorized, switch and wheel assembly 402 may be built in different locations, such as on the top of the handle assembly 122 or on the bottom, etc.

Figure 4B:
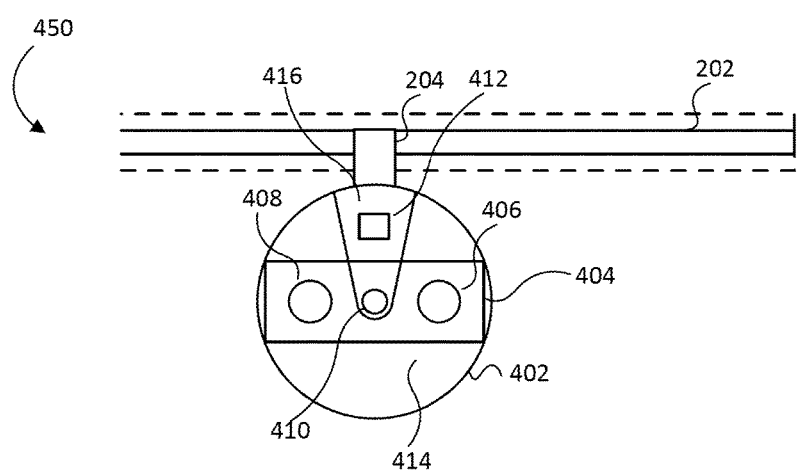
FIG. 4B is an illustration showing a closer view of the mechanics of the motorized switch and wheel assembly, according to some embodiments

With reference now to FIG. 4B, illustration 450 shows a closer view of the mechanics of the motorized switch and wheel assembly 402, according to some embodiments. Similar to the schematics in FIGS. 2 and 3, a rod or cable 202 may be connected to a latch 204, the rod or cable 202 connected to the distal end of the shaft housing 104 and configured to cause articulation of the articulating joint 106. In this case, the latch 204 may be coupled to a hinge on the motorized switch and wheel assembly 402, located behind the assembly, not shown. The wheel portion 416 of the switch and wheel assembly 402 may be configured to rotate along a center hinge 410 of the wheel assembly. A switch 404, similar to the switch in FIG. 2, may be built on top of the wheel assembly. The switch 404 may include two buttons or impressions 406 and 408, whereby a user pressing down on the button so impressions 406 or 408 may cause activation of a motor to rotate the wheel portion 416 of the switch and wheel assembly 402. When the wheel portion 416 is driven to rotate, it may cause the latch 204 to move along in the direction of the rotation via the connected hinge, not shown. The rotation of the wheel portion 416 may therefore cause the rod or cable 202 to traverse back or forth via being connected to the latch 204.

In some embodiments, the switch 404 may be attached to an outer circular housing 414 that may be connected to the wheel portion 416, whereby the outer circular housing 414 would not rotate when the buttons or impressions 406 or 408 are pressed. In some embodiments, the circular housing 414 may not be completely circular, in the sense that a "V" shaped opening may expose part of the rotating wheel portion 416. In this example, the V-shaped opening extends down to the hinge 410. As shown, in some embodiments, the wheel portion 416 also may include a raised ridge 412, here, placed within the V-shaped opening of the circular housing 414. In some embodiments, the rotating wheel portion 416 may be configured to rotate freely via the hinge 410 but for the presence of the raised ridge 412, which may be configured to prevent rotating motion of the wheel portion 416 when a part of the ridge 412 touches the circular housing 414.

In some embodiments, the raised ridge 412 physically preventing further rotation in one direction of the wheel portion 416 may be calibrated to coincide with the articulation joint 106 reaching a maximum angle of articulation. For example, the wheel portion 416 may rotate clockwise until the raised ridge 412 hits the edge of the right side of the V-shaped opening of the circular housing 414, driven by the user pressing on the right button or impression 406. The latch 204 may be configured to correspondingly pull the rod or cable 202 to the right, i.e., proximally toward the user, which in turn may have caused the articulation joint 106 to articulate to the right. That the rotating wheel portion 416 may be further prevented from rotating any more clockwise by the raised ridge 412 may coincide with the articulation joint 106 being fully articulated at a maximum angle to the right. Similarly, as another example, the wheel portion 416 may rotate counterclockwise until the raised ridge 412 hits the edge of the left side of the V-shaped opening of the circular housing 414, driven by the user pressing on the left button or impression 406. The latch 204 may be configured to correspondingly pull the rod or cable to the left, i.e., distally away from the user, which in turn may have caused the articulation joint 106 to articulate to the left. That the rotating wheel portion 416 may be further prevented from rotating anymore counterclockwise by the raised edge 412 may coincide with the articulation joint 106 being fully articulated and a maximum angle to the left.

In this way, the user may have a tactile and visual indicator to determine when the articulation joint 106 (FIG. 1) has reached a maximum articulation angle, even though the user may not be able to see the articulation while the end effector 108 is inside a surgical site. Similarly, if the user is experiencing that the rotating wheel portion 416 is not rotating fully to the point where the ridge 412 has reached either end of the V-shaped opening of the circular housing 414, the user may have additional information suggesting that the lack of articulation may be due to a problem or a malfunction. For example, the user may then determine that the motorized portion of the assembly 402 has failed, or that the articulating end effector 108 has been stopped by a wall or barrier inside the surgical site.

Figure 5A:
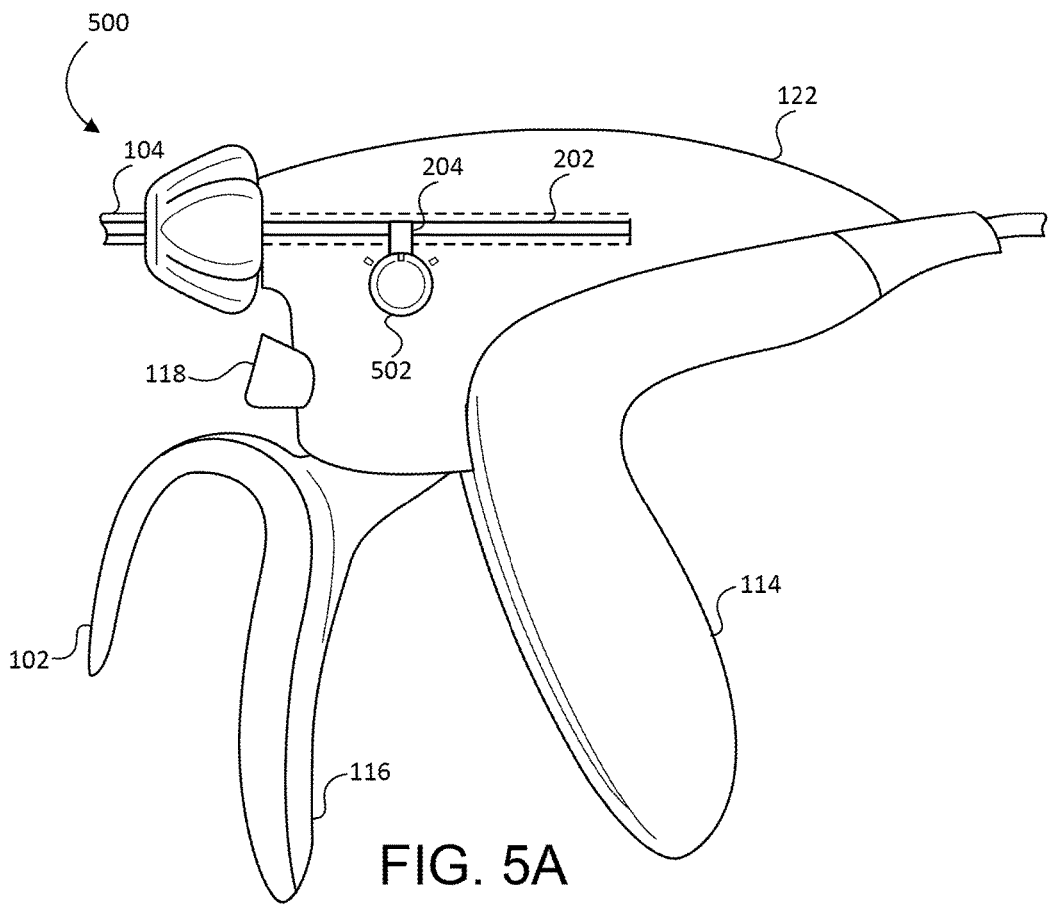
FIG. 5A is an illustration providing yet another example mechanism for aiding the user in determining when the maximum articulation angle of the articulation joint has been reached, according to some embodiments.
Figure 5B:
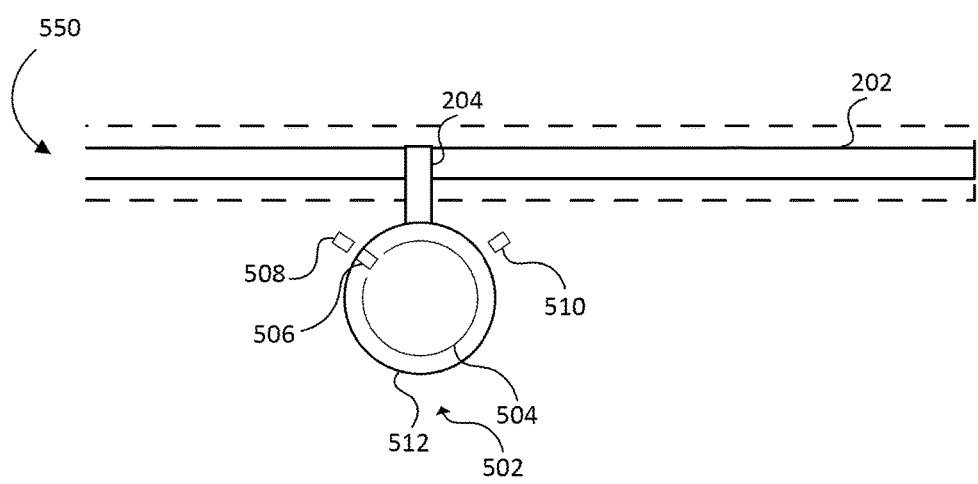
FIG. 5B is an illustration showing a closer view of the mechanics of the electromechanical wheel and sensor assembly, according to some embodiments.

Referring to FIG. 5A, illustration 500 provides yet another example mechanism for aiding the user in determining when the maximum articulation angle of the articulation joint 106 (FIG. 1) has been reached, according to some embodiments. Here, the example handle assembly 122 may include an electro-mechanical wheel and sensor assembly 502 configured to manipulate the articulation joint 106 and provide visual and tactile indicators for when the maximum articulation angles have been reached. In some embodiments, the electromechanical wheel and sensor assembly 502 may be built into the side of the handle assembly 122, as shown, while in other cases the electromechanical wheel and sensor assembly 502 may be built in different locations, such as on the top of the handle assembly 122 or on the bottom, etc.

As shown in FIG. B, illustration 550 shows a closer view of the mechanics of the electromechanical wheel and sensor assembly 502, according to some embodiments. Similar to the schematics in FIGS. 2 and 3, a rod or cable 202 may be connected to a latch 204, the rod or cable 202 connected to the distal end of the shaft housing 104 and configured to cause articulation of the articulation joint 106. In this case, the latch 204 may be coupled to a hinge on the electromechanical wheel and sensor assembly 502, located behind the assembly, not shown. The wheel portion 512 of the electromechanical wheel and sensor assembly 502 may be configured to rotate along a center hinge of the assembly, located behind the while portion 512, not shown. A rotating knob 504 may be built on top of the wheel portion 512 and may be configured to rotate the wheel portion 512 through a user handling and rotating the knob 504. When the wheel portion 512 is driven to rotate, it may cause the latch 204 to move along in the direction of the rotation via the connected hinge, not shown. The rotation of the wheel portion 512 may therefore cause the rod or cable 202 to traverse back or forth via being connected to the latch 204.

In some embodiments, the electromechanical wheel and sensor assembly 502 also may include a series of electrical sensors 506, 508, and 510, configured to interact with each other and provide signals to a user corresponding to when a maximum articulation angle of the articulation joint 106 has been reached. The electrical sensors 508 and 510 may be embedded into the handle assembly 122, in some embodiments. An electrical proximity sensor 506 may be built into the wheel portion 512 or the knob 504, and may be configured to interact with both the sensors 508 and 510. The sensors 506, 508, and 510 may be implemented in various ways, such as utilizing radiofrequency technology, laser technology, or electro magnetic technology as merely some examples.

The electrical proximity sensor 506 may be configured to determine or compute a distance to both the electrical sensors 508 and 510. As previously alluded to, the distances can be measured via RF signal strength, laser distance timing, electromagnetic strength, or other means apparent to those with skill in the art and consistent with the present disclosures. For example, the proximity sensor 506 may transmit a signal in multiple directions toward the sensors 508 and 510. The sensors 508 and 510 may provide back some sort of signal feedback or reflection, the feedback to the proximity sensor 506 of which may indicate how close the proximity sensor 506 is to either the sensor 508 or sensor 510. Thus, as a user rotates the knob 504, the proximity sensor 506 may rotate accordingly. The closest distances of the proximity sensor 506 to the sensors 508 and 510 may be calibrated to correspond to the maximum angles of articulation of the articulation joint 106.

In some embodiments, the electromechanical wheel in sensor assembly 502 may be configured to provide some auditory indicator when the proximity sensor 506 has reached the closest point to either the sensor 508 or sensor 510. Thus, the auditory noise, such as a beep, may inform the user that the articulation joint 106 has reached its maximum articulation angle. In addition, the sensors 508, 510, and even 506, may light up when the proximity sensor 506 has reached the closest point to one of the sensors 508 or 510. Thus, the user also may receive a visual indicator that the articulation joint 106 has reached its maximum articulation angle. In other embodiments, a separate light or sensor may light up somewhere else located on the medical instrument 100 to provide this visual signal, and embodiments are not so limited.

Figure 6A:
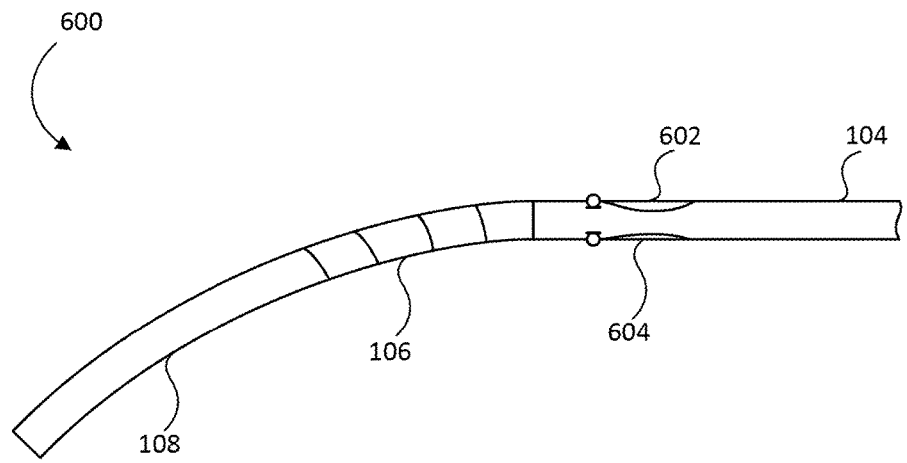
FIG. 6A is an illustration providing an example schematic for automatically straightening the end effector back to its "home" position, according to some embodiments.

Referring to FIG. 6A, illustration 600 provides an example schematic for automatically straightening the end effector back to its "home" position, according to some embodiments. When a user's view of the end effector 108 is obscured, such as when the end effector is inside a surgical site through an incision of a patient, safety precautions should be taken when the user chooses to remove the end effector 108 from the surgical site. For example, if the end effector 108 has been articulated inside the surgical site, then the bent portion of the end effector may hit or get caught in parts of the patient's body if the user tries to remove the end effector before the end effector 108 is straightened out. Trying to remove the end effector 108 before it is straightened, i.e., reached its "home" position, can certainly cause damage to the tissue walls and other parts of the patient. Therefore, it is desirable to ensure that the end effector 108 is always reverted back to the home position whenever the user decides to remove the end effector from the surgical site, even if the user decides to do that inadvertently.

Illustration 600 provides one example of a series of switches for ensuring that the end effector 108 may automatically revert to its home position when being removed from a surgical site, according to some embodiments. Here, the shaft assembly 104 may include two switches 602 and 604, each placed on opposite ends of the shaft assembly 104. In some embodiments, when both switches 602 and 604 are pressed, an electrical or mechanical mechanism coupled to the switches 602 and 604 may cause the end effector 108 and the articulation joints 106 to revert to the home position.

Figure 6B:
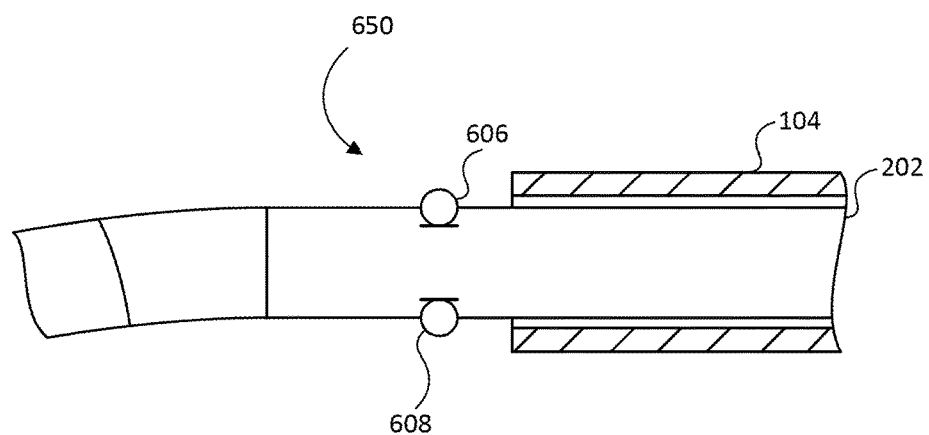
FIG. 6B is an illustration providing another variation of the series of switches configured to automatically revert the articulated end effector back to its home position, according to some embodiments.

With reference to FIG. 6B, illustration 650 provides another variation of the series of switches configured to automatically revert the articulated end effector 108 back to its home position, according to some embodiments. Here, the shaft assembly 104 may extend only out to the straight portions of the shaft or rod 202, and may not cover the articulation joint 106 and the end effector 108. The shaft assembly 104 may therefore act as a cannula of sorts, acting as a cover or sheath for the rod or shaft 202 and some portion of the articulation joint 106. In some embodiments, the end effector and articulation joint 106 may be configured to stretch out beyond the shaft assembly 104 in the distal direction away from the user. For example, the medical instrument 100 may be configured to insert the end effector 108 through an incision into a surgical site of the patient by stretching or pushing the end effector out beyond the shaft assembly 104. In this way, the end effector 108 and the articulation joint 106 may be exposed only when the user intends to use the end effector 108.

As shown in illustration 650, a pair of buttons or switches 606 and 608 may be attached to the rod or shaft 202. When the buttons 606 and 608 are inside the shaft assembly 104, the buttons 606 and 608 may be pressed in due to being pressed against the shaft assembly 104. In some embodiments, the buttons 606 and 608 being pressed in may correspond to the articulation joint 106 being fixed to maintain the home position, i.e., the articulation joint 106 may be disallowed from articulating. Thus, when the end effector 108 (FIGS. 1, 6A) is pushed out or stretched out beyond the shaft assembly 104, the button 606 and 608 may be unimpressed, allowing the articulation joint to maneuver.

Accordingly, when the end effector 108 (FIGS. 1, 6A) is pulled back into the shaft assembly 104, the buttons 606 and 608 will be pressed against the shaft assembly 104, thereby automatically reverting the articulation joint 106 back to the home position. Therefore, the user may be able to insert the end effector 108 into a surgical site, pushing or exposing the end effector 108 beyond the shaft assembly 104. Once the user decides to remove the end effector 108 from the surgical site, he may pull back the end effector 108 out of the surgical site and back into the shaft assembly 104. In so doing, the buttons 606 and 608 may be pressed against the shaft assembly 104, and may cause the joints 106 to revert back to the home position. The example mechanism described herein may allow for a safe exit of the surgical site by preventing the end effector from exiting the surgical site when in any articulated position.

In some embodiments, at least two buttons, such as buttons 606 and 608, may be used to determine when the end effector 108 is being pulled back. For example, if only one button were present, the single button may be pressed due to other factors or forces, such as inadvertently being pressed against a wall or piece of tissue in a surgical site. Having at least two buttons may reduce the chances of accidentally reverting to the home position. In some embodiments, more than two buttons may be used, such as four buttons evenly spaced around the shaft or rod 202.

Referring to FIG. 7A, illustration 700 provides an example mechanism for determining when the articulation joint 106 is in fact articulated, according to some embodiments. Here, the articulation joint 106 may have built a series of sensors or buttons 702 and 704 at each of the joints or links. The sensors or buttons 702 and 704 may be electrically coupled to a sensor processor configured to determine when the articulation joint 106 is in fact articulated. For example, the articulation joint 106 may be articulated in one direction, where the sensors or buttons 704 end up touching their side of the links of the articulation joint 106. Correspondingly, in that same direction, the sensors or buttons 702 also may not be touching the links of the articulation joint 106. One or both of these conditions may signal to the processor coupled to these sensors 702 and 704 that the articulation joint 106 is articulated toward the direction of the sensors 704. Similarly, the articulation joint 106 may be articulated in the other direction, where the sensors or buttons 702 and up touching their side of the legs of the articulation joint 106. Correspondingly, in that same direction, the sensors or buttons 704 also may not be touching the links on their side of the articulation joint 106. One or both of these conditions make signal that the articulation joint 106 is articulated toward the direction of the sensors 702.

FIG. 7B also shows another variation where the shaft assembly 104 is housing the rod or shaft 202, according to some embodiments. Here, the articulation joint 106 and the end effector 108 (FIG. 7A) may be pushed out beyond the shaft assembly 104, the shaft assembly 104 acting like a cannula in that sense.

Figure 8:
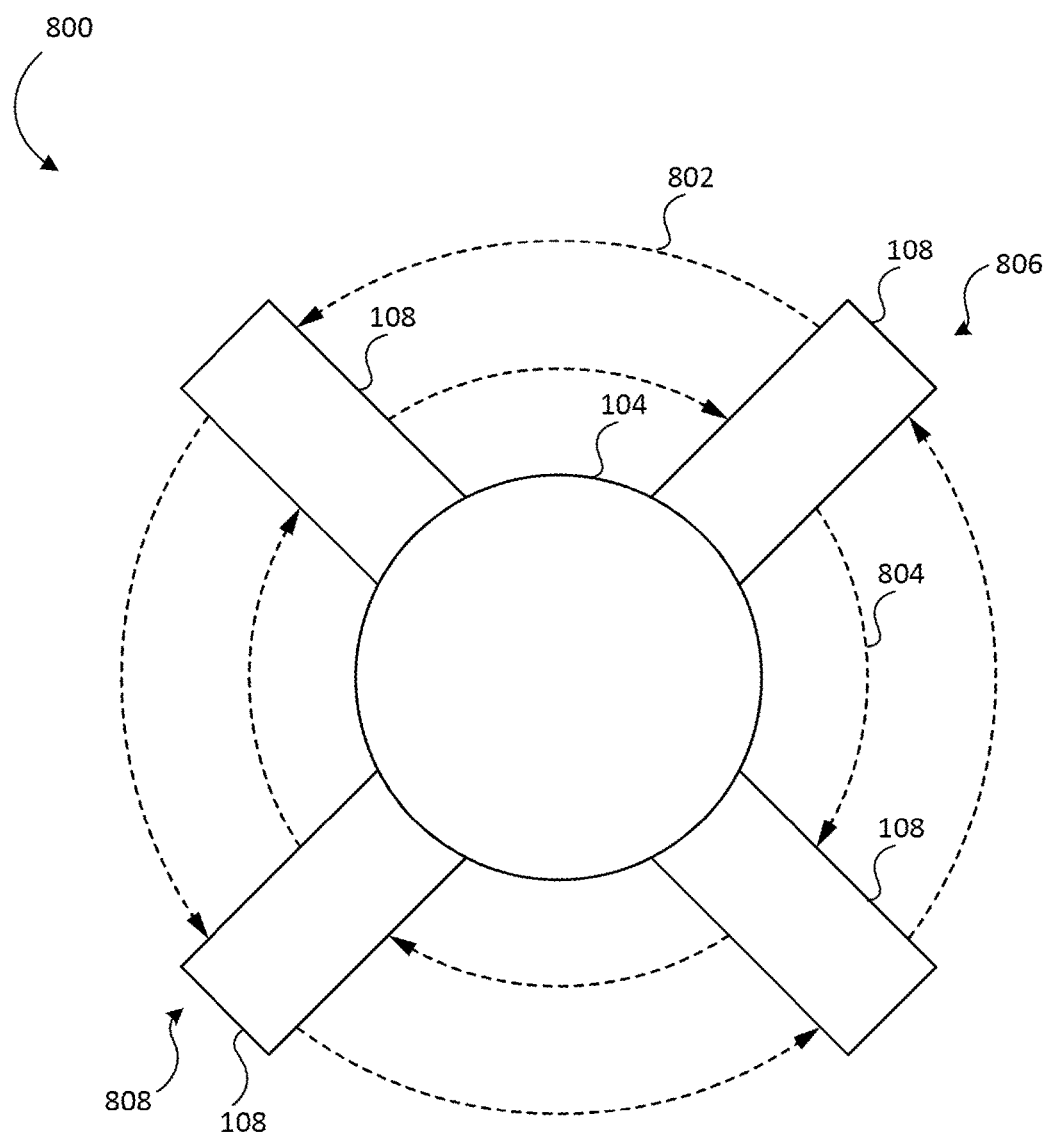
FIG. 8 is an illustration providing a view of the end effector in multiple articulated positions when staring down the shaft assembly, according to some embodiments.

Referring to FIG. 8, illustration 800 provides a view of the end effector 108 in multiple articulated positions when staring down the shaft assembly 104, like "staring down the barrel of a gun." From this perspective, it can be seen that the end effector 108 may be articulated in all 360°. This may be possible due to the medical instrument 100 having two mechanisms for manipulating the end effector 108. That is, the medical instrument 100 may be able to cause articulation of the end effector 108 in at least one direction via the articulation joint 106 (FIG. 1), and also may have a rotation knob 112 (FIG. 1) configured to rotate the shaft assembly 104, which may accordingly guide rotation of the articulation joint 106 and the end effector 108. The rotation knob 112 may allow the end effector to rotate either in clockwise direction 804 or counterclockwise direction 802 from the perspective of illustration 800.

If the articulation joint 106 (FIG. 1) is configured to cause articulation in two directions, then the end effector 108 may be articulated 180° in the opposite direction of whatever direction it is previously oriented. For example, from the perspective of illustration 800, if the end effector 108 is oriented in the top right position 806, then the articulation joint 106 may cause articulation of the end effector 108 to move in the opposite direction, i.e., down to the bottom left position 808, without any rotation from the rotation knob 112. Alternatively, if the end effector 108, starting from position 806, were rotated via the rotation knob 112 by 180°, then the end effector 108 would also end up at the position 808.

However, confusion may arise if the articulation joint 106 (FIG. 1) is guided by buttons or mechanisms that specify an absolute direction for articulating, e.g., a button to articulate to the left or to the right. For example, a mechanism commanding the articulation joint 106 to articulate the end effector 108 "to the right" may result in the end effector 108 be articulated to position 806. Similarly, the mechanism may command the articulation joint 106 to articulate "to the left," thereby causing the end effector 108 articulate to position 808, for example. However, if the rotation knob 112 (FIG. 1) were rotated 180°, now the mechanisms for causing articulation of the articulation joint 106 may cause articulation in the opposite intended direction. It is desirable therefore to maintain the correct direction of articulation no matter how the shaft assembly 104 is rotated. For example, even if the rotation knob 112 caused the shaft assembly 104 to rotate 180°, thereby causing the end effector 108 from being oriented at position 806 to be oriented at position 808, it is desirable for position 806 to always be considered articulating to the right, while being at position 808 should always be considered articulating to the left.

Figure 9:
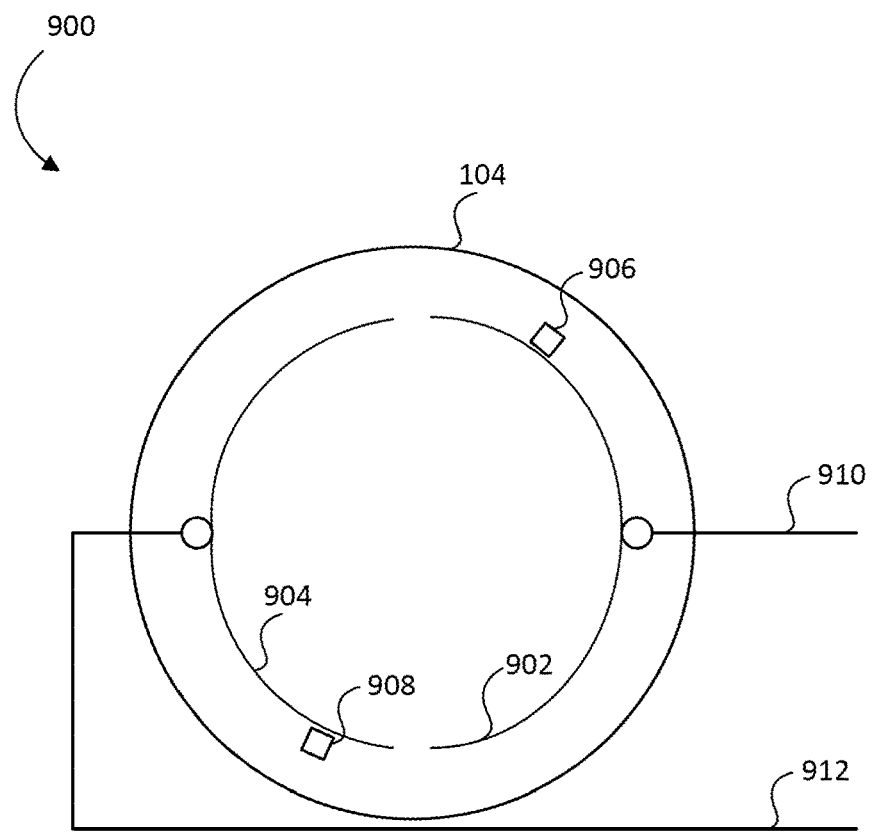
FIG. 9 is an illustration of an example schematic of a circuitry inside the shaft assembly for helping to maintain unambiguous orientation of the articulation angles, according to some embodiments.

Referring to FIG. 9, illustration 900 provides an example schematic of a circuitry inside the shaft assembly 104 for helping to maintain unambiguous orientation of the articulation angles, according to some embodiments. That is, the illustration 900 may help resolve some of the confusion due to the ability to rotate as well as articulate, described in illustration 800 (FIG. 8). Here, embedded inside or attached to shaft assembly 104 may be a commutator ring assembly comprised of two half-ring circuits 902 and 904. The shaft assembly 104 may have attached to it two electrical leads 906 and 908 that may rotate along with the shaft assembly 104. The electrical leads 906 and 908 may be coupled to the half ring circuits 902 and 904, thereby traveling along the half ring circuits whenever the shaft assembly 104 is rotated. The half ring circuit 902 may be electrically coupled via line 910 to an electromechanical or motorized mechanism for causing articulation of the end effector 108, such as any of the mechanisms described in FIGS. 2-5B. The line 910 may be coupled to the button or impression that commands the articulation joint 106 to articulate to the right. Similarly, the half ring circuit 904 may be electrically coupled via line 912 to the mechanism for causing articulation of the end effector 108. The line 912 may be coupled to the button or impression that commands the articulation joint 106 to articulate to the left. Thus, the electrical leads 906 and 908 may rotate along with the shaft assembly 104 and may cross over to the other half ring circuit in order to maintain a proper orientation for articulation.

As discussed herein, any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The invention claimed is:

1. A surgical instrument, comprising:
a handle assembly;
a shaft assembly coupled to a distal end of the handle assembly and comprising a guiding mechanism operatively coupled to an articulation joint and configured to manipulate the articulation joint;
an end effector comprising a surgical tool configured to interface with tissue of a patient;
the articulation joint coupled to the shaft assembly and the end effector and configured to articulate the end effector such that the end effector can be oriented at a different angle relative to the shaft assembly, the articulation joint comprising a first maximum articulation angle in a first direction such that the end effector is prevented from articulating beyond the first maximum articulation angle in the first direction, and a second maximum articulation angle in a second direction such that the end effector is prevented from articulating beyond the second maximum articulation angle in the second direction; and
an articulation control mechanism operatively coupled to the articulation joint through the shaft assembly, comprising:
a latch coupled to the guiding mechanism, the latch comprising a rigid bar configured to uniformly move the guiding mechanism equal in distance as the latch is moved;
a motor operatively coupled to the latch and configured to drive the latch along a longitudinal axis parallel to the shaft assembly; and
a switch coupled to the motor comprising a first and second button and both configured to operate the motor;
and the articulation control mechanism configured to:
control movement of the articulation joint between the first maximum articulation angle and the second maximum articulation angle;
determine that the articulation joint has articulated to the first maximum articulation angle;
provide a first indication that the articulation joint has articulated to the first maximum articulation angle;
determine that the articulation joint has articulated to the second maximum articulation angle; and
provide a second indication that the articulation joint has articulated to the second maximum articulation angle.

2. The surgical instrument of claim 1, wherein:
the first button is configured to direct the motor to drive the latch in a first direction along the longitudinal axis distally away from the handle assembly; and
the second button is configured to direct the motor to drive the latch in a second direction along the longitudinal axis proximally toward the handle assembly.

3. The surgical instrument of claim 2, wherein:
the latch comprises a raised end positioned toward the switch; and
the switch comprises:
a first prominent end positioned at a first edge of the switch near the first button and facing toward the latch; and
a second prominent end positioned at a second edge of the switch near the second button and facing toward the latch.

4. The surgical instrument of claim 3, wherein:
the articulation joint reaches the first maximum articulation angle when the raised end of the latch touches the first prominent end of the switch; and
the articulation joint reaches the second maximum articulation angle when the raised end of the latch touches the second prominent end of the switch.

5. The surgical instrument of claim 1, further comprising:
a first home position switch coupled to the shaft assembly and positioned distal to the handle assembly, the first home position switch disposed to be pressed into the shaft assembly; and
a second home position switch coupled to the shaft assembly and positioned distal to the handle assembly, the second home position switch disposed to be pressed into the shaft assembly;
wherein the articulation joint is positioned distal to both the first home position switch and the second home position switch.

6. The surgical instrument of claim 5, wherein the first home position switch pressed into the shaft assembly simultaneously with the second home position switch pressed into the shaft assembly causes the articulation joint to be articulated to an angle parallel to the shaft assembly.

7. The surgical instrument of claim 1, wherein the articulation joint comprises:
a first link and a second link, the first and second links coupled together by way of a hinge;
a first sensor coupled to a first edge of the first link; and
a second sensor coupled to a second edge of the first link, the second edge located opposite of the hinge.

8. The surgical instrument of claim 7, wherein articulation of the articulation joint in the first direction causes the first sensor to touch the second link, and articulation of the articulation joint in the second direction causes the second sensor to touch the second link.

9. The surgical instrument of claim 1, further comprising a rotation knob coupled to the shaft assembly and configured to rotate the shaft assembly, wherein rotation of the shaft assembly causes rotation of the articulation joint.

10. The surgical instrument of claim 9, wherein the shaft assembly comprises an orientation mechanism configured to maintain orientation of the articulation joint by the articulation control mechanism such that the articulation control mechanism causes the articulation joint to articulate, wherein relative to a first rotation reference point of 0-180 degrees, pressing a first button provides an articulation in a first direction and pressing a second button provides an articulation in a second direction, and wherein relative to a second reference point of 181-360 degrees pressing the first button provides an articulation in the second direction and pressing the second button provides articulation in the first direction.

11. The surgical instrument of claim 10, wherein the orientation mechanism comprises a commutator ring coupled to the shaft assembly and operatively coupled to the articulation control mechanism, such that relative to the first rotation reference point of 0-180 degrees, pressing the first button provides an articulation in the first direction and pressing the second button provides an articulation in the second direction, and wherein relative to the second reference point of 181-360 degrees pressing the first button provides an articulation in the second direction and pressing the second button provides articulation in the first direction.

12. A surgical instrument comprising:
a handle assembly;
a shaft assembly coupled to a distal end of the handle assembly;
an end effector comprising a surgical tool configured to interface with tissue of a patient;
an articulation joint coupled to the shaft assembly and the end effector and configured to articulate the end effector such that the end effector can be oriented at a different angle relative to the shaft assembly, the articulation joint comprising:
a first link and a second link, the first and second links coupled together by way of a hinge;
a first sensor coupled to a first edge of the first link; and
a second sensor coupled to a second edge of the first link, the second edge located opposite of the hinge;
a first home position switch coupled to the shaft assembly and positioned distal to the handle assembly, the first home position switch disposed to be pressed into the shaft assembly;
a second home position switch coupled to the shaft assembly and positioned distal to the handle assembly, the second home position switch disposed to be pressed into the shaft assembly; and
a sensor processor configured to determine when the articulation joint is articulated;
wherein the articulation joint is positioned distal to both the first home position switch and the second home position switch;
wherein articulation of the articulation joint in the first direction causes the first sensor to touch the second link, and articulation of the articulation joint in the second direction causes the second sensor to touch the second link;
wherein when the first sensor touches the second link, the first sensor is configured to transmit a first signal to the sensor processor indicating that the articulation joint is fully articulated in the first direction; and
wherein when the second sensor touches the second link, the second sensor is configured to transmit a second signal to the sensor processor indicating that the articulation joint is fully articulated in the second direction.

13. The surgical instrument of claim 12, wherein the first home position switch pressed into the shaft assembly simultaneously with the second home position switch pressed into the shaft assembly causes the articulation joint to be articulated to an angle parallel to the shaft assembly.

14. The surgical instrument of claim 12, wherein the end effector comprises a trocar.

15. The surgical instrument of claim 12, wherein the end effector comprises a pair of electrosurgical jaws configured to seal tissue using electrosurgical energy.

* * * * *